(12) United States Patent
Ritter et al.

(10) Patent No.: US 7,020,512 B2
(45) Date of Patent: Mar. 28, 2006

(54) METHOD OF LOCALIZING MEDICAL DEVICES

(75) Inventors: Rogers C. Ritter, St. Louis, MO (US); Torrey Munger, Richmond Heights, MO (US); John Rauch, St. Louis, MO (US); Andrew F. Hall, St. Charles, MO (US); Roger N. Hastings, Maple Grove, MN (US)

(73) Assignee: Stereotaxis, Inc., St. Louis, MO (US)

( * ) Notice: Subject to any disclaimer, the term of this patent is extended or adjusted under 35 U.S.C. 154(b) by 214 days.

(21) Appl. No.: 10/047,450

(22) Filed: Jan. 14, 2002

(65) Prior Publication Data
US 2003/0135112 A1    Jul. 17, 2003

(51) Int. Cl.
*A61B 6/00* (2006.01)
(52) U.S. Cl. .................. 600/434; 600/407; 600/423; 600/424
(58) Field of Classification Search ............... 600/407, 600/423, 424, 434
See application file for complete search history.

(56) References Cited
U.S. PATENT DOCUMENTS 5,729,129 A * 3/1998 Acker ............... 324/207.12
5,873,822 A * 2/1999 Ferre et al. ............ 600/407
6,112,111 A * 8/2000 Glantz .................. 600/424
6,298,257 B1 * 10/2001 Hall et al. ............. 600/407
6,474,341 B1 * 11/2002 Hunter et al. .......... 128/899

* cited by examiner

*Primary Examiner*—Ali Imam
*Assistant Examiner*—William Jung
(74) *Attorney, Agent, or Firm*—Harness Dickey & Pierce PLC

(57) ABSTRACT

A method of localizing a medical device inside a patient's body, the method comprising: transmitting ac magnetic signals between a plurality of points of known location outside of the patient's body and a plurality of points on the medical device inside the patient's body, the signals transmitted between at least some of the points comprising at least two different frequencies; and receiving the transmitted ac magnetic signals and processing the received signals to determine the position of the points on the medical device, and thus the location of the medical device, this processing including correcting for the affects of metal in the vicinity by using the transmitted and received signals at different frequencies. In an alternate embodiment, a reference device is provided inside the patients' body, and the medical device is localized relative to the reference catheter. The use of signals comprising at least two frequencies may or may not be used in this relative localization embodiment, but preferably is used at least to localize the reference catheter.

10 Claims, 3 Drawing Sheets

METHOD OF LOCALIZING MEDICAL DEVICES

FIELD OF THE INVENTION

This invention relates to localization of medical device in a patient's body.

BACKGROUND OF THE INVENTION

In medical procedures it is sometimes the case that MRI imaging or fluoroscopic imaging cannot provide all the necessary information needed about the location of a catheter, guidewire, electrode or endoscope inside a patient. For example, in order to accurately navigate medical devices in a patient's body, it is important to be able to accurately localize, i.e., determine the position and/or orientation of, the device. Various methods have been used for localizing medical devices in the body, the processing of x-ray images, electric potential measurement, ultrasonic measurement, and magnetic measurements. A useful method for determining the tip position and orientation of these devices has employed low frequency electromagnetic communication between a transmitter or receiver attached to the tip and a corresponding receiver or transmitter fixed at a position near but outside the patient.

In typical magnetic localization methods, the medical device has at least one receiver, and a transmitter external to the body has a plurality of coils each emitting a different frequency. Sometimes the transmitting coils are separated by significant distances to provide a useful parallax in the vector analysis of the signals from the receiving sensors (which are preferably orthogonal, but at least having orientations which will provide a basis set spanning the space of three dimensions).

There are numerous examples of magnetic localization, including in U.S. Pat. Nos. 5,694,945, 5,846,198, 5,738,096, 5,713,946, 5,833,608, 5,568,809, 5,840,025, 5,729,129, 5,718,241, 5,727,553, 5,391,199, 5,443,489, 5,558,091, 5,480,422, 5,546,951, 5,752,513, 6,092,928, 5,391,199, 5,840,025, U.S. patent application Ser. No. 09/809523, filed Mar. 15, 2001, and published Nov. 29, 2001, as No. 20010045826, and PCT Application No. PC/US01/08389, filed Mar. 16, 2001, and published Sep. 20, 2001, as WO 01/69594 A1, and PCT/GB/01429, published Nov. 16, 2000, as WO 00/68637, the disclosures of all of which are incorporated herein by reference.

While magnetic localization offers a number of advantages, it has suffered from one significant disadvantage—the presence of metal, such as from other medical or imaging equipment, near the operating region impairs the accuracy of magnetic localization. While it is possible through calibration to account for some metal in the operating region, any movement of the metal in the operating region generally requires an extensive and time consuming recalibration to accurately localize the magnetic device.

SUMMARY OF THE INVENTION

The method of the present invention provides for accurate localization of a medical device in the body using magnetic fields, that is not significantly affected by the presence of, or movement of, metal in or near the operating region. Generally, the method comprises transmitting ac magnetic signals between a plurality of points of known location outside of the patient's body and a plurality of points on the medical device inside the patient's body, the signals transmitted between at least some of the points comprising at least two different frequencies; and receiving the transmitted ac magnetic signals and processing the received signals to determine the position of the points on the medical device, and thus the location of the medical device. This processing includes correcting for the affects of metal in the vicinity by using the transmitted and received signals at different frequencies. The inventors have discovered that the effect of metal in and near the operating region is dependent upon the frequency of the magnetic field, and thus by transmitting and measuring at least two frequencies the effect of the metal in and near the operating region can be determined and accounted for, to more accurately determine the position of the medical device.

Thus, the method of this invention provides for fast and accurate localization of medical devices inside the body, which is not substantially impaired by the presence of metal in or near the operating region. These and other features and advantages will be in part apparent and in part pointed out herein after.

DETAILED DESCRIPTION OF THE PREFERRED EMBODIMENT

Generally, the magnetic localization method of this invention employs sensing at multiple frequencies to attempt to correct for errors introduced. There is typically a plurality (e.g., five), transmitters, and at least one receiver. In the case of three signal transmitters and three receivers, it can be seen that if there are 3 frequencies they will provide 3 components measurable on each of the receivers so that vector methods will provide information about the six degrees of freedom desired about the catheter, its three position components and its direction as well as azimuthal orientation.

Figure 1:
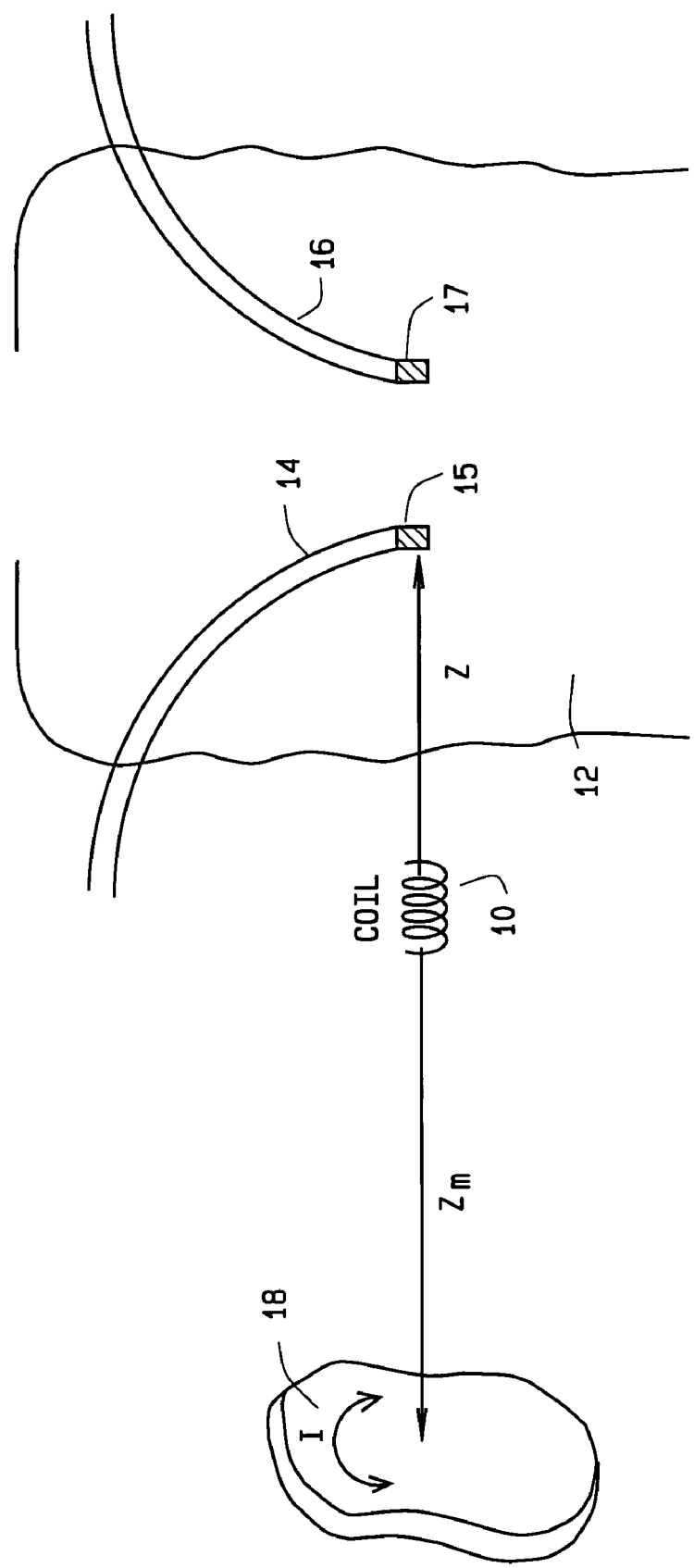
FIG. 1 is schematic drawing of a localization process.

An electromagnetic localization system transmits "low frequency" magnetic fields from a source coil (located outside the body or located in a reference catheter within the body). For purposes of analysis of the signal strength and interference sources, this source coil can be treated as a dipole, and the transmitted dipole field is then given by:

$$B_T(z) = \frac{me^{i\omega t}}{2\pi z^3} \tag{1}$$

where: $B_T(Z)$=the dipole field at a distance z from the transmitting coil m=the dipole moment of the transmitting coil $\omega=2\pi f$, where f is the transmit frequency in Hz t=time in seconds While the transmit field is received at the position, z, of the receiver(s), it also presents a time varying field at the location of metal objects outside of the body, as illustrated in FIG. 1. As shown in FIG. 1. a transmit coil 10 is positioned external to a patient's body 12, in which a medical device 14, having a receiver 15, and a reference catheter 16, having a transmitter 17, are disposed. A representative section of metal 18, having a cross section A and a resistivity $\rho$, is disposed in the vicinity of the transmit coil 10. The This time varying field from the transmit coil 10 generates eddy currents I in the metal object which are driven by the induced voltage given by Lenz' law:

$$V = -d\Phi/dt = -i\omega B_T(-z_m)A \quad (2)$$

where: $Z_m$ = the distance from the transmitter to the metal object

A = the metal object cross-sectional area normal to the flow of eddy currents

The induced voltage drives the eddy currents, which can be found from the ac version of Ohm's law:

$$(i\omega L + r)I = V \quad (3)$$

where: L = inductance of the metal object r = resistance of the metal object or:

$$I = -i\omega B_T(-z_m)A/(i\omega L + r) \quad (4)$$

If we treat the metal object as a magnetic dipole source, it has dipole moment:

$$m_I = \mu_0 I A \quad (5)$$

and the dipole interference field at the receiver coil is given by:

$$B_I(z) = \frac{\mu_0 I A}{2\pi(z_m + z)^3} \quad (6)$$

or from Eq.(4):

$$B_I(z) = \frac{-\mu_0 A^2 B_T(-z_m)}{2\pi L(z_m + z)^3} \frac{i\omega L}{(i\omega L + r)} \quad (7)$$

The fractional change in field at the receiver due to the metal object is defined by:

$$\text{Error} = |B_I(z)/B_T(z)| \quad (8)$$

where the absolute value of the ratio of interference to transmit signals at the receiver is indicated in Eq.(8). Inserting Eqs. (1) and (7) into Eq. (8) yields:

$$\text{Error} = \frac{\mu_0 (z/z_m)^3 \omega L / \sqrt{(\omega L)^2 + r^2}}{2\pi L (z_m + z)^3} \quad (9)$$

Recalling that $\omega = 2\pi f$, we note that in the high frequency limit,

Error $\rightarrow$ independent of f when $\omega L/r \gg 1$

Error $\propto$ f when $\omega L/r \ll 1$

The two frequencies used to correct for the metal signal should be taken at a frequency low enough so that the error is linear in f (i.e. the second case above). In this case, the magnetic fields received at the two frequencies can be written as:

$$B_1 = B_T(z) + c f_1 \quad (10)$$

$$B_2 = B_T(z) + c f_2 \quad (11)$$

from which the constant "c" is evaluated by subtracting the two received signals. The true field, corrected for the presence of metal, is then given by:

$$B_T = B_1 - f_1(B_1 - B_2)/(f_1 - f_2) \quad (11)$$

Equation (11) represents a practical means of correcting the received signals for distortions due to metal, providing that frequencies are used that are below the saturation of the metal ($\omega L/r < 1$). Moving metals that are anticipated in the operating environment can either be subject to measurements to determine the appropriate frequency limit, or mathematically modeled to determine their inductance and resistance.

Another simple technique for eliminating the interference from moving metal is to transmit from the reference catheter shown in FIG. 1. In this case, the separation between the transmitter and receiver is small compared to the distance between the transmitter and the metal residing outside the patient's body. We note from Eq. (9) that when the separation of transmitter and receiver is much less than the distance to the metal object, we have:

$$\text{Error} \propto (z/z_m)^6 \text{ when } z/z_m \ll 1 \quad (12)$$

Thus, when the transmitter is located in the reference catheter and the receiver is in the working catheter, both within the heart, Eq. (12) applies, and the metal objects located outside of the patient body become invisible due to the sixth power reduction in error. In this case, the reference catheter must still be located relative to an external frame of reference. This can be done prior to the medical procedure via non-magnetic locating means, or the interfering metals can be removed during the process of fixing the location of the reference catheter, or the two frequency correction method can be applied to account for metal near the patient during the process of locating the reference catheter.

As discussed above, difficulties with magnetic localization systems are encountered when the transmitting coils are located near metal. At certain frequencies the emitted electromagnetic signals act essentially as oscillating magnetic fields, and therefore such locating methods are often termed "magnetic locators". In the case of a metal sheet behind the transmitter (away from the patient direction), the fields from the transmitters generate currents in the metal sheet which can both reflect (act as an image source behind the metal) and partially absorb (as eddy currents) the oscillating fields, in amounts depending on the frequency. The reflected field combines with the original field to provide a reduced signal. If the location of the sheet metal does not change relative to the transmitting coils, these effects can be calibrated out. However, in many applications there will be metal items whose location will change relative to the patient, for example, where fluoroscopic imaging is used. In this case metal covered imaging plates mounted on a metal C-arm for essentially infinite repositioning around the patient make calibration impractical. Both the closeness of the metal, and its localization, affect the transmission of magnetic signals.

In the present invention, a somewhat standard component method is employed and modified. In this method, commonly used, three separated transmitting coils employ 3 different frequencies to identify the component of each in the signal from each of the orthogonal receiving sensors. The difficulty is that nearby metal will modify the relative magnitudes of each of the 3 frequency signals, thereby causing erroneous location information in the analyzed signal trains. However, unlike prior magnetic localization methods, in the method of the present invention, a multiplicity of frequencies is used, at least two in each transmitting coil. This may be accomplished either by appropriate modulation of a wave source for each given coil, or by separate frequency signals fed to 2 or more separate, closely located coils for each intended source (coil).

In the case of modulation, the demodulation of the received signal will provide the amplitudes of the appropriate different frequency components. Thus, if two frequencies were used for each transmitted signal, they are known and identified in the signal train from each receiving sensor. Each two signals in such a case can be called "partnering" Including geometric effects, they will provide different component magnitudes at the receiving sensor, so their received amplitude differences of the partner frequencies will be in response to the different effect of the metal on them. With judicious choice of frequencies, the effect of the metal can be largely analyzed and accounted for, so as to remove most of the position error it would have caused.

It is well known that the skin depth of penetration of an electromagnetic wave into a conducting and resistive material will vary inversely as the square root of the frequency. [See, e.g. Classical Electrodynamics, 2nd Edition, J. D. Jackson, John Wiley and Sons, Chapter 7, especially sections 7.5 and 7.7, incorporated herein by reference]. Nevertheless, in many cases the metallic material causing the problem will be of complex geometry and thickness, and a direct calculation of relative magnitudes of partnering signals will not permit a complete and accurate correction for the individual signal components. It is not necessary to have an exact total correction for each signal component if all components can be corrected proportionately. Because of this, it is judicious to use a method of ratios.

This method uses similar but discernibly different frequencies for each of the primary frequencies of a partnered pair (or group if more than two frequencies are used in each coil). The other "subsidiary" members of each of the 3 transmitting coils should have appropriate multiples (or sub multiples) of those 3 frequencies. ("Subsidiary" is used simply to differentiate from primary and it does not necessarily mean that the amplitudes will be lower.)

In most cases, the skin depth of the primary 3 frequencies will likely be very much greater than the thickness for a thin interfering metallic sheet, but the effect of the metal on the 3 signals will be similar. Then, in the case where the secondary frequencies are higher they will have a smaller skin depth and be correspondingly affected differently by the metal, as a greater percentage of their signal will be absorbed within the metal. Their summation with the direct waves in the direction towards the patient will be significantly different from that of the primary signals, and a differential frequency-dependent amplitude shift will occur similarly for each of the three transmitted channels. Angular relationships of the coil axes relative to the plane (if such a plane exists) of an interfering metallic sheet will complicate this, but the relationships will still substantially exist in relative magnitudes. With tests and calibrations it is possible to provide simple linear or low-order correcting factors from comparing the relative frequency shifts of members of a coil partner set. These are then applied to the received components resulting from each of the primary signals to provide a correction to the locating algorithm. Providing that the three primary signals are much closer in frequency than they are to their subsidiary partners, the ratio corrections can be effective in reducing positional errors caused by the metal.

Figure 2:
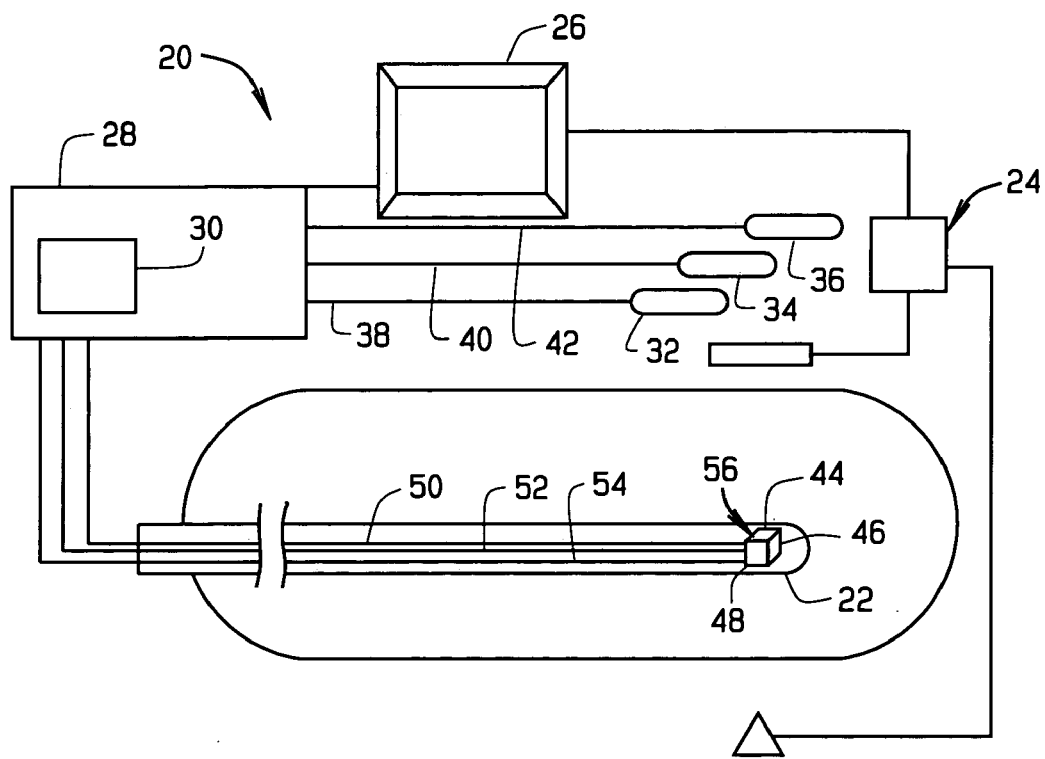
FIG. 2 is a schematic diagram showing a system for implementing a first embodiment of the method of this invention.

A system 20 for implementing a first embodiment of the method of this invention is shown in FIG. 2. The system 20 is adapted for localizing, i.e., determining the location and/or orientation of, a medical device 22 in the operating region O of a patient. The medical device 22 may be any medical device introduced into the body for performing a diagnostic or therapeutic procedure, and can be navigated within the operating region either mechanically or magnetically. An imaging system 24 may be provided for imaging the operating region O. The imaging system 24 may be a conventional x-ray or fluoroscopic imaging system, and an ultrasound imaging system, an MR imaging system or any other suitable imaging system. Images from the imaging system 24 may be displayed on a display 26. Alternatively images from the imaging system 2 may be combined with a representation of the medical device 22 based upon the location of the medical device as determined by the system 20. Still another alternative is to combine pre-operative images, either from imaging system 24 or some other imaging system, with a representation of the medical device 22 based upon the location of the medical device as determined by the system 20.

The system 20 includes a controller 28, having a microprocessor 30. The display 26 may be connected to the controller 28. A plurality of transmitters, disposed in known fixed relation to the operating region O of the patient, are provided outside of the patient's body. In this preferred embodiment there are three transmitters 32, 34, and 36, connected by lines 38, 40, and 42, respectively, to controller 28. There is also at least one receiver in the distal end of the medical device 22. In this preferred embodiment, there are three receivers 44, 46, and 48, connected by leads 50, 52, and 54 respectively, to controller 28. These receivers may be mounted on a fixture 56 in orthogonal relation to each other. Of course, the number of transmitters and the number of receivers can vary, it may be desirable to provide five or more transmitters and just a single receiver, or any combination of transmitters and receivers that can be conveniently provided and which provide sufficient information for localization.

The controller 28 causes the transmitters 32, 34, and 36, to transmit ac magnetic signals that are received by the receivers 44, 46, and 48. Preferably, the ac magnetic signal sent by each transmitter is different from the ac magnetic signal sent by the other transmitters. Thus, a total of nine different signals are provided for use in localizing the receivers and the medical device 22 on which they are mounted: (1) the signal from transmitter 32 received by receiver 44; (2) the signal from transmitter 32 received by receiver 46; (3) the signal from transmitter 32 received by receiver 48; (4) the signal from transmitter 34 received by receiver 44; (5) the signal from transmitter 34 received by receiver 46; (6) the signal from transmitter 34 received by receiver 48; (7) the signal from transmitter 36 received by receiver 44; (8) the signal from transmitter 36 received by receiver 46; and (9) the signal from transmitter 36 received by receiver 48.

In accordance with this invention, the ac magnetic signal transmitted by each transmitter 32, 34, and 36 preferably includes at least two frequencies. This can be accomplished by using a modulated signal, for example a frequency modulated signal or an amplitude modulated signal, or it can be accomplished by changing the signal over time. The receivers 44, 46, and 48 receive the signals and leads 50, 52, and 54 conduct the signals to the controller 22. The controller processes the signals received at both frequencies, and can adjust for frequency-dependent interference, such as is caused by the presence of, or movement of, metal in the vicinity of the operating region O. The processor can accurately localize the medical device 22, and can display an image of the medical device 22 on a preoperative or current image of the operating region. The position information can also be used in a navigation control system, for example in an automated magnetic surgery system, wherein a magnetic navigation system that orients the device, coupled with a manual or automatic advancer, automates that process of navigating the medical device 22 to a selected location inside the patient.

Figure 3:
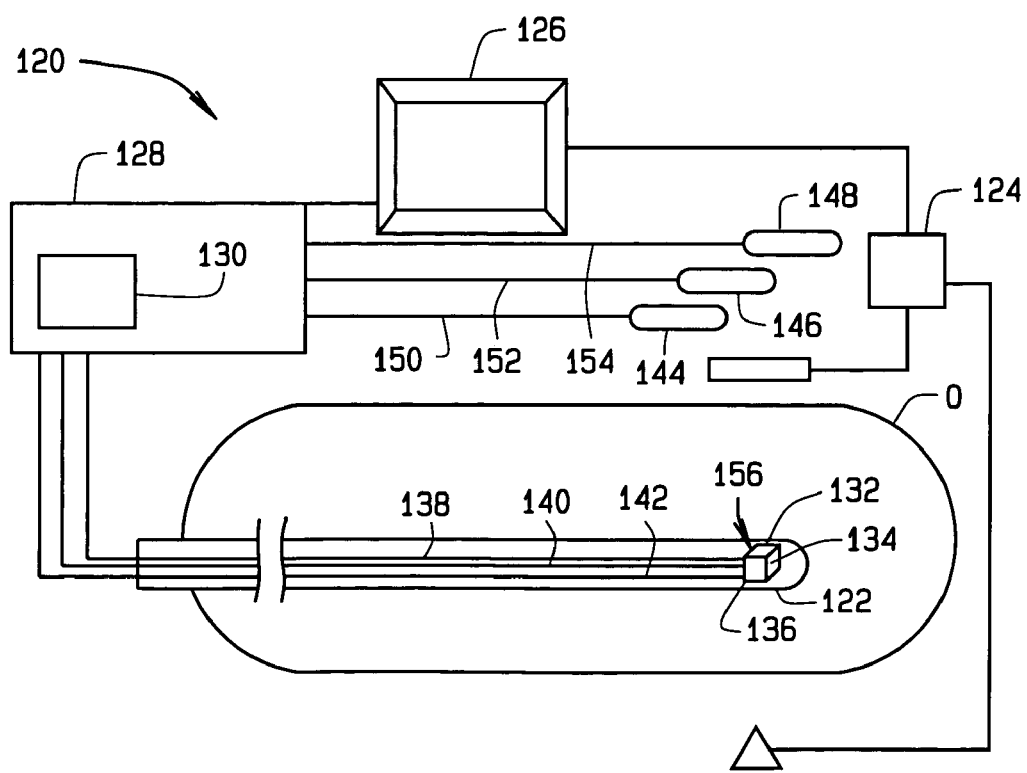
FIG. 3 is a schematic diagram showing a system for implementing an alternate mode of the first embodiment of the method of this invention.

A system 120 for implementing an alternate mode of the first embodiment of the method of this invention is shown in FIG. 3. The system 120, like the system 20, is adapted for localizing, i.e., determining the location and/or orientation of, a medical device 122 in the operating region O of a patient, and is similar to system 20 and corresponding parts are identified with corresponding numerals.

An imaging system 124 may be provided for imaging the operating region O. The imaging system 124 may be a conventional x-ray or fluoroscopic imaging system, and an ultrasound imaging system, an MR imaging system or any other suitable imaging system. Images from the imaging system 124 may be displayed on a display 126. Alternatively images from the imaging system 124 may be combined with a representation of the medical device 122 based upon the location of the medical device as determined by the system 120. Still another alternative is to combine pre-operative images, either from imaging system 124 or some other imaging system, with a representation of the medical device 122 based upon the location of the medical device as determined by the system 120.

The system 120 includes a controller 128, having a microprocessor 130. The display 126 may be connected to the controller 128. At least one transmitter is disposed on the device 122. In system 120 there are three transmitters 132, 134, and 136, connected by leads 138, 140, and 142, respectively, to controller 128. These transmitters may be mounted on a fixture 156 in orthogonal relation to each other. There are also a plurality of receivers in known positions outside the patient. In system 120 there are three receivers 144, 146, and 148, connected by lines 150, 152, and 154 respectively, to controller 128. These receivers may be mounted in known, fixed relation to the patient and the operating region. Of course the number of transmitters and receivers could be varied, for example there could be a single transmitter, and five or more receivers, or any combination of transmitters and receivers that can be conveniently provided and which provide sufficient information for localization.

The controller 128 causes the transmitters 132, 134, and 136, to transmit ac magnetic signals that are received by the receivers 144, 146, and 148. Preferably, the ac magnetic signal sent by each transmitter is different from the ac magnetic signal sent by the other transmitters. Thus, a total of nine different signals are provided for use in localizing the transmitters and the medical device 122 on which they are mounted: (1) the signal from transmitter 132 received by receiver 144; (2) the signal from transmitter 132 received by receiver 146; (3) the signal from transmitter 132 received by receiver 148; (4) the signal from transmitter 134 received by receiver 144; (5) the signal from transmitter 134 received by receiver 146; (6) the signal from transmitter 134 received by receiver 148; (7) the signal from transmitter 136 received by receiver 144; (8) the signal from transmitter 136 received by receiver 146; and (9) the signal from transmitter 136 received by receiver 148.

In accordance with this invention, the ac magnetic signal transmitted by each transmitter 132, 134, and 136 preferably includes at least two frequencies. This can be accomplished by using a modulated signal, for example a frequency modulated signal or an amplitude modulated signal, or it can be accomplished by changing the signal over time. The receivers 144, 146, and 148 receive the signals and lines 150, 152, and 154 conduct the signals to the controller 128. The controller processes the signals received at both frequencies, and can adjust for frequency-dependent interference, such as is caused by the presence of, or movement of, metal in the vicinity of the operating region O. The processor can accurately localize the medical device 122, and can display an image of the medical device 122 on a preoperative or current image of the operating region. The position information can also be used in a navigation control system, for example in an automated magnetic surgery system, wherein a magnetic navigation system that orients the device, coupled with a manual or automatic advancer, automates that process of navigating the medical device 122 to a selected location inside the patient.

Figure 4:
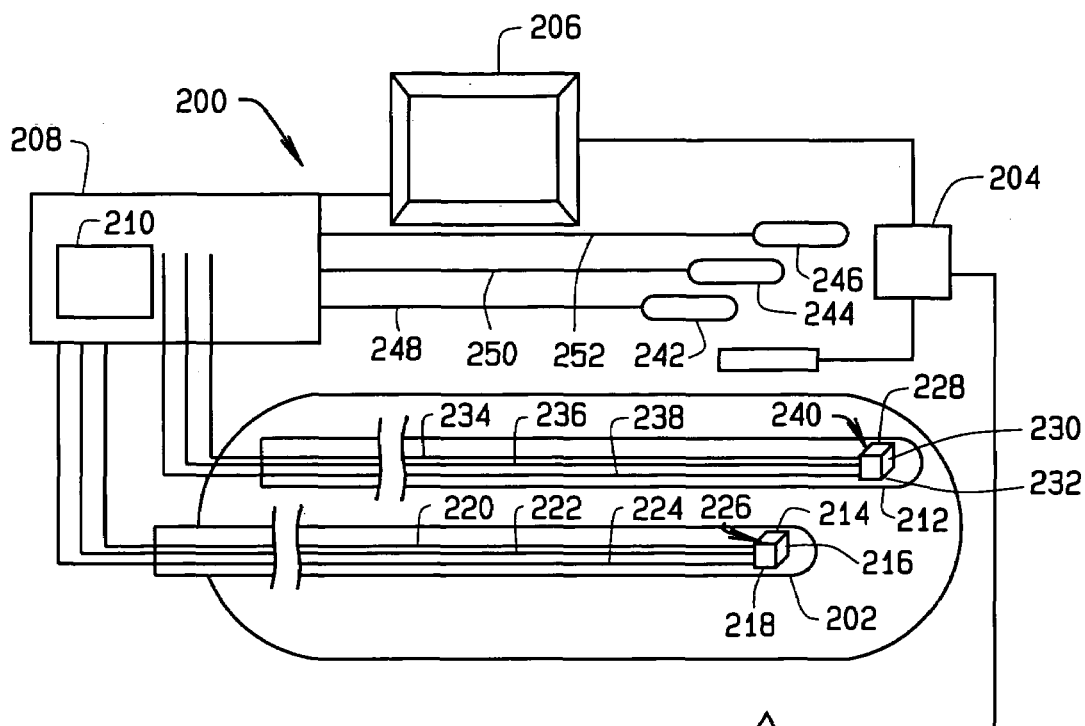
FIG. 4 is a schematic diagram showing a system for implementing a second embodiment of the method of this invention.

A system 200 for implementing a second embodiment of the method of this invention is shown in FIG. 4. The system 200 is adapted for localizing, i.e., determining the location and/or orientation of, a medical device 202 in the operating region O of a patient. The medical device 202, like devices 22 and 122 discussed above, may be any medical device introduced into the body for performing a diagnostic or therapeutic procedure, and can be navigated within the operating region either mechanically or magnetically. An imaging system 204 may be provided for imaging the operating region O. The imaging system 204, like system 24 discussed above may be a conventional x-ray or fluoroscopic imaging system, and an ultrasound imaging system, an MR imaging system or any other suitable imaging system. Images from the imaging system 204 may be displayed on a display 206. Alternatively images from the imaging system 204 may be combined with a representation of the medical device 202 based upon the location of the medical device as determined by the system 200. Still another alternative is to combine pre-operative images, either from imaging system 204 or some other imaging system, with a representation of the medical device 202 based upon the location of the medical device as determined by the system 200.

The system 200 includes a controller 208, having a microprocessor 210. The display 206 may be connected to the controller 208. A plurality of transmitters, disposed in known fixed relation in the operating region O of the patient, are provided on a reference catheter 212. In this preferred embodiment there are three transmitters 214, 216, and 218, connected by leads 220, 222, and 224, respectively, to controller 208. The transmitters may be mounted on a fixture 226 in orthogonal relation to each other. There is also at least one receiver in the distal end of the medical device 202. In this preferred embodiment, there are three receivers 228, 230, and 232, connected by leads 234, 236, and 238 respectively, to controller 208. These receivers may be mounted on a fixture 240 in orthogonal relation to each other. Of course the number of transmitters and receivers could be varied, for example there could be five or more transmitters, and one receiver, or any combination of transmitters and receivers that can be conveniently provided and which provide sufficient information for localization.

The controller 208 causes the transmitters 214, 216, and 218, to transmit ac magnetic signals that are received by the receivers 228, 230, and 232. Preferably, the ac magnetic signal sent by each transmitter is different from the ac magnetic signal sent by the other transmitters. Thus, a total of nine different signals are provided for use in localizing the receivers and the medical device 202 on which they are mounted: (1) the signal from transmitter 214 received by receiver 228; (2) the signal from transmitter 214 received by receiver 230; (3) the signal from transmitter 214 received by receiver 232; (4) the signal from transmitter 216 received by receiver 228; (5) the signal from transmitter 216 received by receiver 230; (6) the signal from transmitter 216 received by receiver 232; (7) the signal from transmitter 218 received by receiver 228; (8) the signal from transmitter 218 received by receiver 230; and (9) the signal from transmitter 218 received by receiver 232.

In accordance with this invention, the ac magnetic signal transmitted by each transmitter 214, 216, and 218 preferably includes at least two frequencies. This can be accomplished by using a modulated signal, for example a frequency modulated signal or an amplitude modulated signal, or it can be accomplished by changing the signal over time. The receivers 228, 230, and 232 receive the signals and leads 234, 236, and 238 conduct the signals to the controller 208. The controller processes the signals received at both frequencies, and can adjust for frequency-dependent interference, such as is caused by the presence of, or movement of, metal in the vicinity of the operating region O. The processor can accurately localize the medical device 202, relative to the reference catheter 212.

Once the location of the medical device 202 is determined relative to the reference catheter 212, the position of the medical device in the operating region O can be determined by localizing the reference catheter. The localization of the reference catheter 212 can be done once at the start of the procedure, when the reference catheter is positioned, or it can be done periodically during the procedure, so that movement or migration of the reference catheter does not affect the accuracy of the localization of the medical device in the operating region. The reference catheter can be localized using x-ray, fluoroscopic, or MR image processing, electrical potential localization, ultrasound localization, or even magnetic localization. When the reference catheter is localized prior to the procedure, metal in and around the operating region is not typically an issue, but if it is, or if the reference catheter is localized during the procedure, the methods of this invention can be used to localize the reference catheter independent of metal in and around the operating region. For example, receivers 242, 244, and 246 can be provided in known fixed locations outside of the patient, and connected to controller 208 by lines 248, 250, and 252. As described above, the three transmitters 214, 216, and 218, on the reference catheter 212 connected by leads 220, 222, and 224, respectively, to controller 208. The controller 208 causes the transmitters 214, 216, and 218, to transmit ac magnetic signals that are received by the receivers 242, 244, and 246. Preferably, the ac magnetic signal sent by each transmitter is different from the ac magnetic signal sent by the other transmitters. Thus, a total of nine different signals are provided for use in localizing the transmitters 214, 216, and 218, and thus the reference catheter 212 on which they are mounted: (1) the signal from transmitter 214 received by receiver 242; (2) the signal from transmitter 214 received by receiver 244; (3) the signal from transmitter 214 received by receiver 246; (4) the signal from transmitter 216 received by receiver 242; (5) the signal from transmitter 216 received by receiver 244; (6) the signal from transmitter 216 received by receiver 246; (7) the signal from transmitter 218 received by receiver 242; (8) the signal from transmitter 218 received by receiver 244; and (9) the signal from transmitter 218 received by receiver 246. It should be noted that transmitters 214, 216, and 218 may be operable as receivers, and rather than receivers 242, 244, and 246 in fixed, known positions relative to the patient, transmitters could be provided instead. Alternatively, in addition to transmitters 214, 216, and 218, the reference catheter could be provided with separate receivers. Further, the number of transmitters and receivers could be varied, so long as the combination of transmitters and receivers can be conveniently provided and provide sufficient information for localization In accordance with this invention, the ac magnetic signal transmitted by each transmitter 214, 216, and 218 preferably includes at least two frequencies. This can be accomplished by using a modulated signal, for example a frequency modulated signal or an amplitude modulated signal, or it can be accomplished by changing the signal over time. The receivers 242, 244, and 246 receive the signals and leads 248, 250, and 252 conduct the signals to the controller 208. The controller processes the signals received at both frequencies, and can adjust for frequency-dependent interference, such as is caused by the presence of, or movement of, metal in the vicinity of the operating region O. The processor can accurately localize the reference catheter relative to a fixed frame of reference outside the patient. With the medical device 202 localized relative to the reference catheter 212, and the reference catheter 212 localized relative to a fixed frame of reference outside the patient, the medical device is localized relative to the fixed frame of reference. In fact, given the typically small distances between the reference catheter 212 and the medical device 202, as compared to the relatively larger distances between the reference catheter 212 and the receivers 242, 244, and 246, and the fact that interfering metal is much further away from the medical device 202 and reference catheter 212 than the receivers 242, 244, and 246, the multiple frequency methods of this invention may only need to be employed in localizing the reference catheter. The localizing of the medical device relative to the reference catheter may be largely unaffected by metal outside the body.

Figure 5:
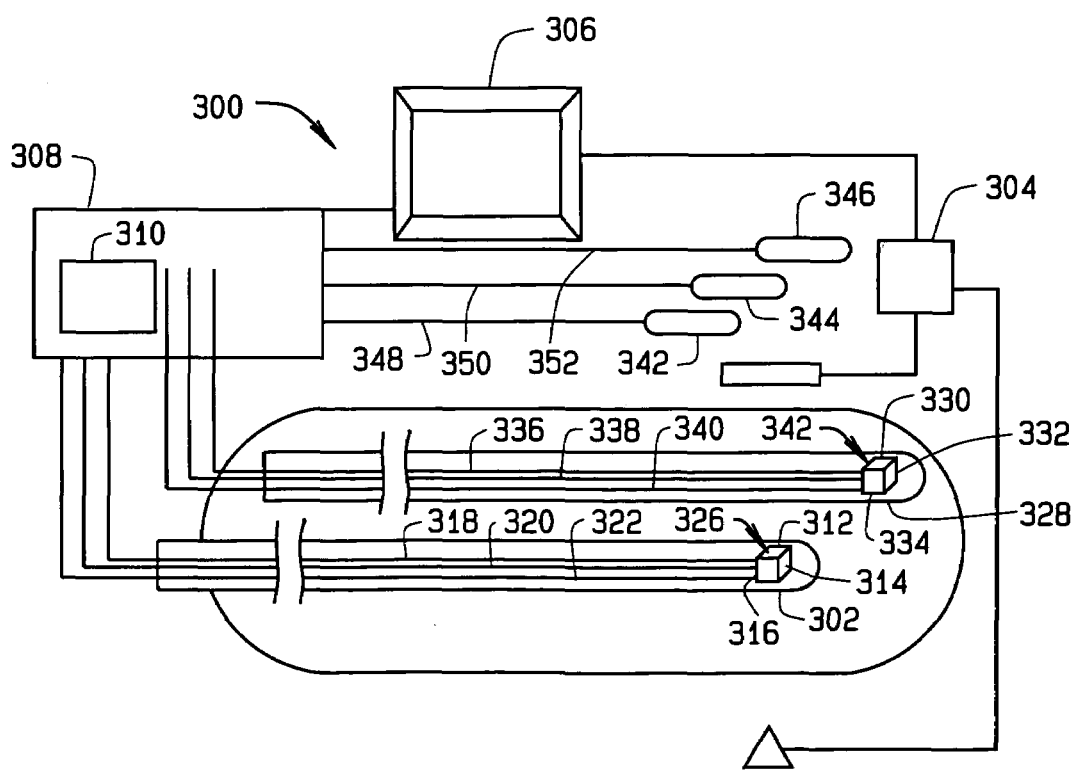
FIG. 5 is a schematic diagram showing a system for implementing an alternate mode of the second embodiment of the method of this information.

A system 300 for implementing an alternate mode of a second embodiment of the method of this invention is shown in FIG. 5. The system 300 is adapted for localizing, i.e., determining the location and/or orientation of, a medical device 302 in the operating region O of a patient. The medical device 302, like devices 22, 122, and 202 discussed above, may be any medical device introduced into the body for performing a diagnostic or therapeutic procedure, and can be navigated within the operating region either mechanically or magnetically. An imaging system 304 may be provided for imaging the operating region O. The imaging system 304, like system 24, and 204 discussed above may be a conventional x-ray or fluoroscopic imaging system, and an ultrasound imaging system, an MR imaging system or any other suitable imaging system. Images from the imaging system 304 may be displayed on a display 306. Alternatively images from the imaging system 304 may be combined with a representation of the medical device 302 based upon the location of the medical device as determined by the system 300. Still another alternative is to combine pre-operative images, either from imaging system 304 or some other imaging system, with a representation of the medical device 302 based upon the location of the medical device as determined by the system 300.

The system 300 includes a controller 308, having a microprocessor 310. The display 306 may be connected to the controller 308. A plurality of transmitters are provided on the medical device 302. In this preferred embodiment, there are three transmitters 312, 314, and 316 on the distal end of the medical device 302, connected by leads 318, 320, and 322, respectively, to controller 308. These transmitters may be mounted on a fixture 326, in mutually orthogonal relation to each other. There are also a plurality of receivers on the distal end of reference catheter 328. In this preferred embodiment, there are three receivers 330, 332, and 334 on the distal end of the reference catheter 328, connected by leads 336, 338, and 340, respectively to the controller 308. The receivers may be mounted on a fixture 342, in mutually orthogonal relation to each other. Of course, the number of transmitters and the number of receivers can vary, it may be desirable to provide five or more transmitters and just a single receiver, or any combination of transmitters and receivers that can be conveniently provided and which provide sufficient information for localization.

The controller 308 causes the transmitters 312, 314, and 316, to transmit ac magnetic signals that are received by the receivers 330, 332, and 334. Preferably, the ac magnetic signal sent by each transmitter is different from the ac magnetic signal sent by the other transmitters. Thus, a total of nine different signals are provided for use in localizing the transmitters 312, 314, and 316 and the medical device 302 on which they are mounted: (1) the signal from transmitter 312 received by receiver 330; (2) the signal from transmitter 312 received by receiver 332; (3) the signal from transmitter 312 received by receiver 334; (4) the signal from transmitter 314 received by receiver 330; (5) the signal from transmitter 314 received by receiver 332; (6) the signal from transmitter 314 received by receiver 334; (7) the signal from transmitter 316 received by receiver 330; (8) the signal from transmitter 316 received by receiver 332; and (9) the signal from transmitter 316 received by receiver 334.

In accordance with this invention, the ac magnetic signal transmitted by each transmitter 312, 314, and 316 preferably includes at least two frequencies. This can be accomplished by using a modulated signal, for example a frequency modulated signal or an amplitude modulated signal, or it can be accomplished by changing the signal over time. The receivers 330, 332, and 334 on the reference catheter 328 receive the signals and leads 336, 338, and 340 conduct the signals to the controller 308. The controller 308 processes the signals received at both frequencies, and can adjust for frequency-dependent interference, such as is caused by the presence of, or movement of, metal in the vicinity of the operating region O. The processor can accurately localize the medical device 302, relative to the reference catheter 328.

Once the medical device 302 is determined relative to the reference catheter 328, the position of the medical device in the operating region O can be determined by localizing the reference catheter. The localization of the reference catheter 328 can be done once at the start of the procedure, when the reference catheter is positioned, or it can be done periodically during the procedure, so that movement or migration of the reference catheter does not affect the accuracy of the localization of the medical device in the operating region. The reference catheter 328 can be localized using x-ray, fluoroscopic, or MR image processing, electrical potential localization, ultrasound localization, or even magnetic localization. When the reference catheter is localized prior to the procedure, metal in and around the operating region is not typically an issue, but if it is, or if the reference catheter is localized during the procedure, the methods of this invention can be used to localize the reference catheter independent of metal in and around the operating region. For example, transmitters 342, 344, and 346 can be provided in known fixed locations outside of the patient, and connected to controller 28 by lines 348, 350, and 352. The controller 308 causes the transmitters 342, 344, and 346, to transmit ac magnetic signals that are received by the receivers 330, 332, and 334. Preferably, the ac magnetic signal sent by each transmitter is different from the ac magnetic signal sent by the other transmitters. Thus, a total of nine different signals are provided for use in localizing the receivers 330, 332, and 334, and thus the reference catheter 328 on which they are mounted: (1) the signal from transmitter 342 received by receiver 330; (2) the signal from transmitter 342 received by receiver 332; (3) the signal from transmitter 342 received by receiver 334; (4) the signal from transmitter 344 received by receiver 330; (5) the signal from transmitter 344 received by receiver 332; (6) the signal from transmitter 344 received by receiver 334; (7) the signal from transmitter 346 received by receiver 330; (8) the signal from transmitter 346 received by receiver 332; and (9) the signal from transmitter 346 received by receiver 334. It should be noted that receivers 330, 332, and 334 may be operable as transmitters, and rather than transmitters 342, 344, and 346 in fixed, known positions relative to the patient, receivers could be provided instead. Alternatively, in addition to receivers 330, 332, and 334, the reference catheter 328 could be provided with separate transmitters. Further, the number of transmitters and receivers could be varied, so long as the combination of transmitters and receivers can be conveniently provided and provide sufficient information for localization.

In accordance with this invention, the ac magnetic signal transmitted by each transmitter 342, 344, and 346 preferably includes at least two frequencies. This can be accomplished by using a modulated signal, for example a frequency modulated signal or an amplitude modulated signal, or it can be accomplished by changing the signal over time. The receivers 330, 332, and 334 on the reference catheter 328 receive the signals and leads 336, 338, and 340 conduct the signals to the controller 308. The controller processes the signals received at both frequencies, and can adjust for frequency-dependent interference, such as is caused by the presence of, or movement of, metal in the vicinity of the operating region O. The processor can accurately localize the reference catheter 328 relative to a fixed frame of reference outside the patient. With the medical device 302 localized relative to the reference catheter 328, and the reference catheter 328 localized relative to a fixed frame of reference outside the patient, the medical device is localized relative to the fixed frame of reference. In fact, given the typically small distances between the reference catheter 328 and the medical device 302, as compared to the relatively larger distances between the reference catheter 328 and the transmitters 342, 344, and 346, and the fact that interfering metal is much further away from the medical device 302 and reference catheter 328 than the transmitters 342, 344, and 346, the multiple frequency methods of this invention may only need to be employed in localizing the reference catheter. The localizing of the medical device relative to the reference catheter may be largely unaffected by metal outside the body.

Localization Utilizing a Reference Device

The basic operating principle for most localization schemes is to emit a localization signal from a source and receive that signal with a detector. Where these schemes differ is in the localization signal used, the placement of the source and detector, and the algorithms used to discern the detector's position and orientation relative to the source. However as discussed above with respect to FIGS. 4 and 5, it is possible to use a system of relative localization to localize a medical device relative to reference catheter in the body in a known location. Because the distance between the reference catheter and the medical device is relatively small, interference from metal in and around the operating region, most of which is spaced significantly further than the separation between the reference catheter and the medical device, is reduced.

A primary distinction between relative magnetic localization and conventional magnetic localization is the location of the reference. In conventional magnetic localization, the reference (either a transmitter or receiver) is located outside of the body, where its position and orientation are fixed in space. With relative localization, the reference (either a transmitter or receiver) is located inside of the body, and usually will be fixed to the anatomy of interest.

In relative localization, the reference device is preferably an inter-lumen device with electromagnetic source coils. The number and orientation of the coils is device dependent. Additionally, the reference device may have some mechanism by which it may be anchored to the anatomy of interest. This anchoring mechanism could be, for example, a screw, balloon, jaws, barb, or mechanical wedging device. Each localizable device will also be an inter-lumen device with electromagnetic coils that are capable of receiving the electromagnetic signal from the source device. As with the reference device, the number and orientation of the electromagnetic coils in the localizable device will be device specific. (Of course, transmitters could be provided on the localizable devices, and receivers could be provided on the reference catheters).

Relative magnetic localization offers several benefits over conventional magnetic localization, including: reducing the effect of interfering external magnetic fields (if present) on the accuracy of the localization, because the source and detector can be placed much closer together; diminishing the influence of large metal objects on the electromagnetic signal generated by the source, improving the localization accuracy and moving metal immunity; reducing the signal strength required for localization to be much less than conventional magnetic localization because of the decreased distance between the source and the detector allow the signal strength; and localizing a relative to a (potentially moving) anatomical structure.

As described and illustrated above, a reference device or catheter containing a transmitter or receiver is introduced into the body, and anchored in a position, for example with a screw. For example in the case of a cardiac procedure, the reference device might be placed into the right atrium and attached to the septal wall via the screw. A localizable medical device, such as an electrophysiology catheter or other device, containing a corresponding receiver or transmitter in its distal tip. This scenario would be capable of providing six degrees of localization (x, y, and z positions; as well as x, y, and z axial rotations). The implementation of the localization hardware would determine the number of devices that could be localized, as well as the accuracy of their localization.

As described above, in the situation where localization is required to be relative to a specific coordinate system, an extra localization detector could be placed external to the anatomy and used to determine the transformation between the desired coordinate system and the localized coordinate system. The additional localization detector would have to be placed in a known position and orientation relative to the desired coordinate system. The design of this detector will dictate the maximum distance it may be placed from the source device to achieve a specific accuracy.

It is also possible to localize devices relative to the coordinate system of a bi-planar fluoroscopy system, providing that the two fluoroscopy planes can provide mutually exclusive views (this is optimal when the two fluoroscopy planes are orthogonal). By locating the tip of the reference device in both of the fluoroscopic views, and knowing the physical arrangement of the imaging system, it is possible to identify the localization source's position and orientation relative to the coordinate system of the imaging system.

It is also possible to register preoperative images (e.g., from ultrasound, CT, MRI, PET, or other medical imaging systems) to the localization coordinate system, by computing a transformation between the image set and localization coordinate systems. The tip of the reference could be designed to allow its position and orientation to be uniquely determinable in standard medical imaging modalities. If the image was acquired in a gated fashion, such as with cardiac gating in CT, the same gating could be performed on the localization of devices by the localization system. This helps to ensure that the positions and orientations of the localized devices are known relative to the preoperative image.

One approach to registration is to fix the localization reference device in the anatomy of interest prior to performing the scan. Once the reference is found in the 3D image set, and its orientation determined, it is a simple matter to calculate the coordinate system transform between the image set and localization coordinate systems.

An alternative approach to placing the reference in the patient prior to acquiring the scan, is to map out the anatomy of interest. The mapping process requires the placement of the reference, and consists of the movement of the reference device to boundary points inside the anatomy of interest and the storage of these localized point coordinates. These points can then be evaluated in the preoperative image and translation and rotation transformations applied to the set of collected points until a fit is made between the collected points and the image data. A good fit will require many points; fewer points can be used if they are positioned in key unique features of the anatomy. If the image set was acquired in a gated fashion, then the localization must be performed with the same gating, in order to get accurate results.

In relative localization, ultrasonic signals, ac magnetic signals, or dc magnetic signals can be used. There are also a number of combinations of the placement of transmitters and receivers that can be implemented. For example, the transmitters can be on the reference catheter and the receivers on the medical device, or the transmitters can on the medical device and the receivers on the reference catheter, or transmitters and receivers can be provided on both the reference catheter and the medical device. Moreover, the mode of localizing the reference catheter can be the same (i.e., the reference catheter transmits to both the reference device and the medical device, or receives from both the reference device and medical device), or different (i.e., the reference catheter transmits to the medical device, but receives from the at least one reference device, or receives from the medical device and transmits to the reference device).

The inventors have determined that a triaxial coil set about 5 mm in length inside the distal tip of an 8 French reference catheter can transmit a signal to a triaxial receiver coil at the tip of an 8 French receiver catheter located up to 2 inches away, with sufficient signal strength to localize the receiver coil to within 1 mm. Eddy currents in the transmitter or receiver catheters introduce less than 1% error, and intermediate electrodes on other catheters give even smaller errors. This assumes 1 Watt of transmit power, which will not heat the transmit catheter. Water cooling of the transmitter coil allows the signal voltage to be increased up to five fold, reducing the error by four fifths, which is comparable to using a smaller receiver coil volume.

What is claimed is:

1. A method of localizing a medical device at a procedure site in the body, comprising:
   securing a reference catheter having at least one transmitter in the patient's body near the procedure side;
   transmitting magnetic signals comprising at least two frequencies between the reference catheter and at least one reference device of known position in an external frame of reference outside the body to determine the position of the reference catheter with respect to the external frame of reference;
   introducing the medical device into the patient's body;
   transmitting magnetic signals between the medical device and the reference catheter and processing the signals to determine the position of the device relative to the reference catheter, wherein at least some of the magnetic signals transmitted between the reference catheter and the medical device comprise at least two frequencies; and
   determining the position of the medical device relative to the external reference frame.

2. The method according to claim 1 wherein the signals are transmitted by the reference catheter and received by the reference device.

3. The method according to claim 1 wherein the signals are transmitted by the reference device and received by the reference catheter.

4. The method according to claim 1 wherein signals are both transmitted and received by the reference catheter and the reference device.

5. The method according to claim 1 wherein signals are transmitted by the reference catheter to the medical device.

6. The method according to claim 1 wherein signals are transmitted by the medical device to the reference catheter.

7. The method according to claim 1 wherein signals are transmitted from the at least one reference device to the reference catheter, and wherein signals are transmitted from the medical device to the reference catheter.

8. The method according to claim 1 wherein signals are transmitted from the reference catheter to the at least one reference device, and wherein the signals are transmitted from the reference catheter to the medical device.

9. The method according to claim 1 wherein signals are transmitted from the at least one reference device to the reference catheter, and wherein the signals are transmitted from the reference catheter to the medical device.

10. The method according to claim 1 wherein the signals transmitted are at least one of ac magnetic or dc magnetic.

* * * * *